United States Patent [19]

Reardan et al.

[11] Patent Number: 5,157,099

[45] Date of Patent: Oct. 20, 1992

[54] ACTIVATED POLYMERS AND CONJUGATES THEREOF

[75] Inventors: Dayton T. Reardan, Hercules; Dane A. Goff, Menlo Park, both of Calif.

[73] Assignee: Xoma Corporation, Berkeley, Calif.

[21] Appl. No.: 806,690

[22] Filed: Dec. 12, 1991

Related U.S. Application Data

[62] Division of Ser. No. 717,431, Jun. 19, 1991, Pat. No. 5,103,039.

[51] Int. Cl.$^5$ .................. C08G 18/32; C07C 275/24; C07C 275/40
[52] U.S. Cl. .................. 528/68; 528/69; 435/181; 530/405; 564/51; 564/149; 564/159; 564/163; 564/443; 564/50
[58] Field of Search ............ 564/50, 51, 48, 45; 528/68, 69; 435/181; 530/405

[56] References Cited

U.S. PATENT DOCUMENTS

| | | | |
|---|---|---|---|
| 2,714,607 | 8/1955 | Matter | 560/50 |
| 2,714,610 | 8/1955 | Matter | 560/50 |
| 3,789,073 | 1/1974 | Narayahan et al. | 564/168 |
| 4,179,337 | 12/1979 | Davis et al. | 435/181 |
| 4,515,981 | 5/1985 | Otani et al. | 560/50 |
| 4,537,945 | 8/1985 | Otani et al. | 560/50 |
| 5,041,477 | 8/1991 | Hays | 564/48 |

*Primary Examiner*—Carolyn Elmore
*Assistant Examiner*—Shailendra Kumar

*Attorney, Agent, or Firm*—Townsend and Townsend

[57] ABSTRACT

Macromolecular species such as enzymes, proteins, drugs, and solid supports which contain reactive carbonyl, groups or groups which are readily converted to reactive carbonyl groups are modified by reaction with a compound of the formula

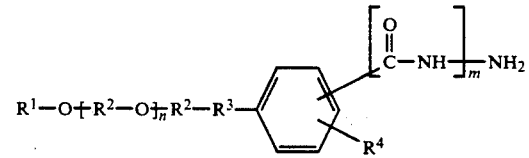

in which $R^1$ is H, $C_1$-$C_{20}$ alkyl, phenyl, ($C_1$-$C_{10}$ alkyl)-substituted phenyl, or phenyl-substituted $C_1$-$C_{10}$ alkyl; $R^2$ is $C_2$-$C_5$ alkylene or ($C_1$-$C_4$ alkoxy)-substituted $C_2$-$C_5$ alkylene; $R^3$ is

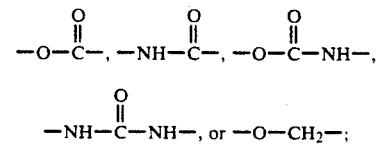

$R^4$ is H or $C_1$-$C_4$ alkyl; n is at least 5; and m is zero or 1.

12 Claims, No Drawings

ACTIVATED POLYMERS AND CONJUGATES THEREOF

This is a division of application Ser. No. 07/717,431 filed Jun. 19, 1991, now U.S. Pat. No. 5,103,039.

BACKGROUND OF THE INVENTION

This invention relates to the modification of macromolecular species such as proteins, injectable compounds in general and solid supports, by conjugation with polymers. This invention further relates to activated polymers for use in such conjugation.

Polymers, such as polyethylene glycol, polypropylene glycol and analogs, have been coupled to enzymes, drugs, polypeptides and poly(amino acids) of various kinds to modify their immunological and biochemical properties. Among the desirable changes achieved in this manner are the reduction or elimination of immunogenicity, induction of tolerance, an increased resistance to proteolytic degradation in the serum, a controlled or gradual release (in the case of a drug) arising from a slow rate of enzyme-induced dissociation from the polymer, an alternation in the tissue distribution (in the case of a drug, for instance) by varying its water solubility or its molecular size, a change in surface characteristics (in the case of a solid support), and, in the case of an enzyme, for instance, a change in kinetics, a shift in the pH and temperature optima, and altered reactivity to substrate.

The goal of conjugation in most cases is to modify certain properties while retaining others (such as drug or enzyme activity, for instance) substantially unchanged. In many cases, this selectivity varies with the locus of the conjugation site on the macromolecule, and the number of sites on a single macromolecule which take part in the conjugation. Most conjugations to date have been made at amino moieties on drugs or enzymes. In many cases, this presents a problem due to the wide distribution of reactive amino groups on the molecule. The result is often a lack of control over the degree or rate of conjugation, and a substantial interference with the desired activity of the macromolecule. In an immunoglobulin, for instance, where the antigen-binding portions bear a large number of amino groups, conjugation at these groups can cause interference with the immunoglobulin's ability to bind antigen.

SUMMARY OF THE INVENTION

Novel compositions and methods are provided herein for the modification of macromolecular species by conjugation with polymers at reactive carbonyl groups on the species. Derivatized polymers for use in accordance with the invention are those of the formula

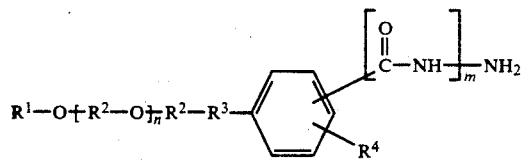

in which $R^1$ is H or a protecting group which will prevent a coupling reaction from occurring at the end of the polymer to which it is attached; examples of such protecting groups are $C_1$-$C_{20}$ alkyl, phenyl, ($C_1$-$C_{10}$ alkyl)-substituted phenyl, or phenyl-substituted $C_1$-$C_{10}$ alkyl;

$R^2$ is $C_2$-$C_5$ alkylene or ($C_1$-$C_4$ alkoxy)-substituted $C_2$-$C_5$ alkylene;

$R^3$ is

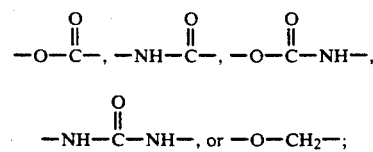

$R^4$ is H or $C_1$-$C_4$ alkyl;

n is at least 5; and m is zero or 1.

Further included within the scope of this disclosure are analogs and homologs of the above, varying for example in the identity and position of the substituents and in other ways readily occurring to those skilled in the art, which may be considered as equivalents of the above.

Throughout this specification, the terms "alkyl," "alkoxy," "alkylene" and the like denote both straight-chain and branched-chain structures.

Conjugates formed as the reaction product of the macromolecular species with these derivatized polymers are those having the formula

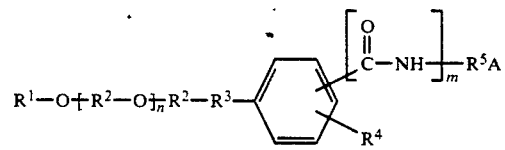

in which $R^1$, $R^2$, $R^3$, $R^4$, n and m are defined above, $R^5$ is either —N= or —NH—, and A is the residue of the macromolecular species. The term "residue" is used herein in its conventional sense, meaning that portion of the molecule remaining after loss of the atoms removed from it in the process of conjugation. The residue may also vary with the type of linkage as represented by the $R^5$ group. Likewise, the choice between the two alternatives for $R^5$ will depend in part upon the reactive group on the macromolecular species and its neighboring atoms, and in part upon the conjugation reaction. The various possibilities and the appropriate selection among them in any given case will be readily apparent to those skilled in the art.

The macromolecular species will be one bearing a carbohydrate or carboxyl group available for conjugation. Carbohydrate groups are first converted to aldehydes to prepare them for the reaction. This is done by conventional means well known to those skilled in the art. Examples include the use of galactose oxidase or periodate under mild conditions.

Within the scope of these formulas, certain embodiments are preferred. For example, $R^1$ is preferably H or $C_1$-$C_{10}$ alkyl, with $C_1$-$C_5$ alkyl more preferred and methyl particularly preferred. Likewise, $R^2$ is preferably $C_2$-$C_5$ alkylene, with —$CH_2$—$CH_2$— (ethylene) and —$CH(CH_3)$—$CH_2$— (isopropylene) more preferred, and ethylene particularly preferred. Similarly, $R^4$ is preferably H or methyl, with H particularly preferred. In further preferred embodiments, the group

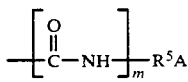

occupies either a meta- or para- position with respect to R³ on the phenyl ring. The integer n is preferably 10 to 1000, and most preferably 50 to 200.

The following are examples of activated polymers within the scope of Formula I:
ω-Methoxy-α-(p-aminobenzoyl)polyethylene glycol
α-Methoxy-α-(m-aminobenzoyl)polyethylene glycol [alternative nomenclature: poly(oxy-1,2-ethanediyl), α-(4-aminobenzoyl)-ω-methoxy]
ω-Methoxy-α-(p-aminobenzamido)polyethylene glycol
ω-Methoxy-α-(o-aminobenzamido)polyethylene glycol
ω-Methoxy-α-(p-aminophenylaminocarbonyl)-polyethylene glycol
ω-Methoxy-α-(m-aminophenylaminocarbonyl)-polyethylene glycol
ω-Methoxy-α-(p-aminophenylaminocarbonylamino)-polyethylene glycol
ω-Methoxy-α-(o-aminophenylaminocarbonylamino)-polyethylene glycol
ω-Methoxy-α-(p-hydrazinocarbonyl)benzamidopolyethylene glycol
ω-Methoxy-α-(p-hydrazinocarbonyl)benzoyl polyethylene glycol
ω-Methoxy-α-(m-hydrazinocarbonyl)benzoyl polyethylene glycol
ω-Ethoxy-α-(p-aminoenzoyl)polyethylene glycol
ω-Propoxy-α-(m-aminobenzoyl)polyethylene glycol
ω-Phenoxy-α-(p-aminobenzamido)polyethylene glycol
ω-n-Dodecycloxy-α-(m-aminophenylaminocarbonyl)-polyethylene glycol
ω-n-Octadecycloxy-α-(p-aminophenylaminocarbonylamino)polyethylene glycol
ω-p-(n-Octyl)phenoxy-α-(p-aminobenzoyl)polyethylene glycol
ω-p-(n-Nonyl)phenoxy-α-(p-aminobenzoyl)polyethylene glycol

DETAILED DESCRIPTION OF THE INVENTION

The compounds of the present invention are prepared by conventional techniques well known among those skilled in the art, selected in accordance with the desired substituent groups as listed above.

Compounds where R³ terminates in a carbonyl group at the end adjacent to the phenyl group may be prepared by reacting a protected polyalkylene glycol with an appropriately substituted benzoyl halide. To achieve the —NH—C(O)— linkage, the protected polyalkylene glycol will be substituted with an amino group at the α-position. To achieve the —O—C(O)— linkage, the protected polyalkylene glycol can be used directly.

Compounds where R³ terminates in an amino group at the end adjacent to the phenyl group may be prepared by reacting a protected polyalkylene glycol with an appropriately substituted phenylisocyanate. To achieve the —NH—C(O)—NH— linkage, an α-amino-substituted protected polyalkylene glycol is reacted with the phenyl isocyanate. To achieve the —O—CH₂— linkage, the protected polyalkylene glycol is reacted with the appropriately substituted benzyl halide.

Attachment of the protecting group may be achieved in any conventional manner as well. A number of suitable mono-protected polyalkylene glycols are commercially available and others are readily prepared by those skilled in the art.

The macromolecular species to which the activated polymers attach may be any of a wide variety of species containing a carbonyl group available for reaction with an amine, or species containing groups which are readily convertible to reactive carbonyl groups, such as carbohyrate moieties. The macromolecular species may be enzymes, coenzymes, immunoglobulins, immunotoxins and other conjugates, proteins and drugs in general, and polymeric solid supports such as microbeads and chromatographic support media. Enzymes and coenzymes are of particular interest. Examples are L-asparaginase, uricase, and catalases. The coupling reaction itself may be effected in accordance with conventional procedures for Schiff base reactions or amide bond formation, well known to those skilled in the art.

The following examples are offered for purposes of illustration, and are intended neither to define nor limit the invention in any manner. These examples illustrate the preparation of compounds within the scope of the present invention. In these examples, the following abbreviations are used:

IR: infrared spectra; values given in cm$^{-1}$; "s"=strong, "vs"=very strong, "w"=weak, "sh"=shoulder.

TLC: thin-layer chromatography; values given in $R_f$ (ratio to the front),

UV/VIS: ultraviolet/visible spectroscopy range; values given in relative absorption.

EXAMPLE 1

A. Preparation of ω-Methoxy-α-(p-nitrobenzoyloxy)-polyethylene Glycol.

This compound was prepared as a precursor to ω-methoxy-α-(p-aminobenzoyl)polyethylene glycol, whose preparation is described in part B which follows.

ω-Methoxy-α-hydroxypolyethylene glycol with an average molecular weight of approximately 5000 (0.90 g, 0.18 mMol) and p-nitrobenzoyl chloride (34 mg, 0.18 mMol) were refluxed in 25 mL of dry methylene chloride for 5.5 hours, then stirred for two and one-half days at room temperature. Solvent was then removed in vacuo and the residue dried in vacuo to give a white solid weighing 0.85 g. IR analysis yielded the following:

IR: 1722 (C=O), 1530 (NO₂).

B. Preparation of ω-Methoxy-α-(p-aminobenzoyl)polyethylene Glycol.

The product of part A of this Example (0.85 g) was dissolved in warm methanol (100 mL) and treated with 10% Pd/C (200 mg, caution: sparks) and hydrogenated at 1 atmosphere for three days. The catalyst was filtered off and the solvent removed in vacuo to give a white solid weighing 0.72 g. The structure was confirmed as that of ω-methoxy-α-(p-aminobenzoyloxy)polyethylene glycol by TLC and IR as follows:

TLC (90/10 CH₂Cl₂/CH₃OH): one rather streaky spot at $R_f$ 0.22–0.37 (I₂ visible, not strongly UV positive); ninhydrin positive (starting material is ninhydrin negative).

IR: 1695 (C=O), 1600, no absorbance at 1530 cm$^{-1}$.

This material (55 mg) was dialyzed against H₂O (3500 molecular weight cutoff) for 16 days at 4° C., then lyophilized. The UV/VIS spectrum and IR were basically unchanged as a result.

EXAMPLE 2

A. Preparation of ω-Methoxy-α-(m-nitrobenzamido)-polyethylene Glycol

This compound was prepared as a precursor to ω-methoxy-α-(m-aminobenzamido)polyethylene glycol, whose preparation is described in part B which follows.

ω-Methoxy-α-aminopolyethylene glycol with an average molecular weight of approximately 5000 (5.0 g, 1 mMol) in 75 mL of dry toluene was treated with 2.0 g (10.7 mMol) of m-nitrobenzoyl chloride at 80° C. in a constant temperature bath under a nitrogen atmosphere for 18 hours. The reaction mixture was concentrated to dryness in vacuo, then dissolved in $H_2O$ and dialyzed against $H_2O$ using 3500 molecular weight cutoff dialysis tubing for five days. A small amount of crude material which did not dissolve well in $H_2O$ remained at all times. The aqueous solution was concentrated to dryness in vacuo at 50° C. and dried in vacuo at room temperature to give a beige-colored solid weighing 2.4 g. Its structure was verified as that of the title compound by IR, UV/VIS and TLC as follows:

IR (KBr): 2890 (s), 1730 (C=O), 1540 ($NO_2$), 1475, 1370, 1350, 1285, 1250, 1120 (vs), 975, 850.

UV/VIS: ($CH_3OH$) 254 (0.18), 218 (0.48); ($CH_2Cl_2$) 254 (0.906), 220 (0.12).

B. Preparation of ω-Methoxy-α-(m-aminobenzamido)-polyethylene Glycol.

The product of part A of this Example (2.4 g) was dissolved in 100 mL of warm ethanol, cooled, treated with 500 mg of 10% Pd/C and hydrogenated at 20 psi on a Parr apparatus at room temperature for 16.5 hours. (The warming is necessary, with cooling before adding the catalyst. On occasion, the starting material will crystallize upon cooling.) The catalyst was filtered off and the filtrate evaporated in vacuo to give a white solid weighing 1.98 g (82% yield). The structure was confirmed as that of the title compound by IR, UV/VIS and TLC as follows:

IR (KBr): 2880 (s), 1720 (w, C=O), 1470, 1365, 1345, 1285, 1115 (vs), 970, 845 (note that the peak at 1540 is no longer present).

UV/VIS: ($CH_3OH$) 316 (0.068), 224 (0.815); ($CH_2Cl_2$) 314 (0.247), 238 (1.09).

TLC (4/1 $C_2H_5OH$/25% concentrated aqueous $NH_3$): $R_f$ 0.6–0.7, one spot, gives blue fluorescence (the nitro starting material does not fluoresce); the product gives a weak reaction with ninhydrin.

EXAMPLE 3

A. Preparation of ω-Methoxy-α-(p-nitrophenylaminocarbonyl)-polyethylene Glycol.

This compound was prepared as a precursor to ω-methoxy-α-(m-aminophenylaminocarbonyl)polyethylene glycol, whose preparation is described in part B which follows.

ω-Methoxy-α-hydroxy polyethylene glycol with an average molecular weight of approximately 5000 (0.90 g, 0.018 mMol) was dissolved in 25 mL of dry $CH_2Cl_2$ with two drops of triethylamine. p-Nitrophenylisocyanate (30 mg, 0.18 mMol) was then added and the mixture refluxed overnight. After 26 hours, the solvent was removed in vacuo to give a yellow waxy solid weighing 0.78 g, whose structure was verified as that of the title compound by IR as follows:

IR (KBr): 1730 (carbamate), 1600, 1510 (sh), plus the usual absorptions associated with polyethylene glycol (1468, 1360, 1245, 1280, 1240, 1110, 965, 845). Absorption at 2270 was not observed, indicating that no unreacted p-nitrophenyl isocyanate remained.

B. Preparation of ω-Methoxy-α-(p-aminophenylaminocarbonyl)-polyethylene Glycol The product of part A of this Example (0.78 g) was dissolved in 100 mL of a warm 1:1 mixture of methanol and tetrahydrofuran, and hydrogenated at 1 atmosphere with 10% Pd/C for 65 hours. The catalyst was filtered off and the solvent removed in vacuo to give a pale brown solid weighing 0.72 g, whose structure was confirmed as that of the title compound by TLC and IR as follows:

TLC (90/10 $CH_2Cl_2$/$CH_3OH$): $R_f$ 0.4 (faint), 0.23–0.3 (major), 0.18 (minor). All three spots were ninhydrin positive.

IR (KBr): 1720, 1525 (w) plus the usual absorptions associated with polyethylene glycol (see Part A) Note: (1) The peak at 1600 $cm^{-1}$ in the starting material (1595 in p-nitrophenylisocyanate), assigned to $NO_2$ is gone; and (2) C=O shows a shift from 1730 to 1720 $cm^{-1}$ similar to examples tabulated by D. Dolphin and A. Wiese, *Tabulation of Infrared Spectral Data*, Wiley & Sons (1977).

The foregoing is offered primarily for purposes of illustration. It will be readily apparent to those skilled in the art that variations and modifications of the structures and procedures described herein may be made without departing from the spirit and scope of the invention.

What is claimed is:

1. A compound having the formula

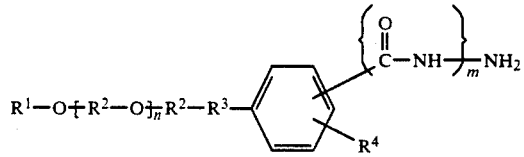

in which

R$^1$ is a member selected from the group consisting of H, $C_1$–$C_{20}$ alkyl, phenyl, ($C_1$–$C_{10}$ alkyl)-substituted phenyl, and phenyl-substituted $C_1$–$C_{10}$ alkyl;

R$^2$ is a member selected from the group consisting of $C_2$–$C_5$ alkylene and $C_1$–$C_4$ alkoxy-substituted $C_2$–$C_5$ alkylene;

R$^3$ is

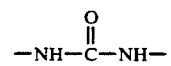

R$^4$ is a member selected from the group consisting of H and $C_1$–$C_4$ alkyl;

n is at least 5;

m is zero or 1; and the group

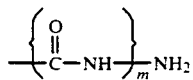

occupies either a meta- or a para-position with respect to $R^3$ on the phenyl ring.

2. A compound in accordance with claim 1 in which $R^1$ is a member selected from the group consisting of H and $C_1$-$C_{10}$ alkyl.

3. A compound in accordance with claim 1 in which $R^1$ is a member selected from the group consisting of H and $C_1$-$C_5$ alkyl.

4. A compound in accordance with claim 1 in which $R^1$ is methyl.

5. A compound in accordance with claim 1 in which $R^2$ is $C_2$-$C_5$ alkylene.

6. A compound in accordance with claim 1 in which $R^2$ is a member selected from the group consisting of $-CH_2-CH_2-$ and $-CH(CH)_3-CH_2-$.

7. A compound in accordance with claim 1 in which $R^2$ is $-CH_2-CH_2-$.

8. A compound in accordance with claim 1 in which the

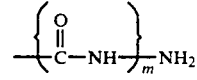

group occupies a para-position with respect to $R^3$ on the phenyl ring.

9. A compound in accordance with claim 1 in which $R^4$ is a member selected from the group consisting of H and methyl.

10. A compound in accordance with claim 1 in which $R^4$ is H.

11. A compound in accordance with claim 1 in which n is 10 to 1000.

12. A compound in accordance with claim 1 in which n is 50 to 200.

* * * * *